United States Patent
Itoh

(10) Patent No.: US 6,898,296 B2
(45) Date of Patent: May 24, 2005

(54) SPECIMEN PROCESSING SYSTEM

(76) Inventor: Teruaki Itoh, 5-25, Kokaihommachi, Kumamoto-shi, Kumamoto-ken (JP)

( * ) Notice: Subject to any disclaimer, the term of this patent is extended or adjusted under 35 U.S.C. 154(b) by 564 days.

(21) Appl. No.: 09/878,357

(22) Filed: Jun. 12, 2001

(65) Prior Publication Data

US 2002/0025064 A1 Feb. 28, 2002

(30) Foreign Application Priority Data

Jun. 23, 2000 (JP) ........................................ 2000-189659

(51) Int. Cl.[7] .............................................. G06K 9/00
(52) U.S. Cl. .................... 382/100; 382/128; 250/201.3; 356/39
(58) Field of Search ............................... 382/100, 128, 382/133, 134, 154; 118/52; 250/201.3; 356/39; 359/390, 396; 436/183, 63; 600/309

(56) References Cited

U.S. PATENT DOCUMENTS

| | | | | |
|---|---|---|---|---|
| 4,363,781 A | * | 12/1982 | Akamatsu et al. | ............ 422/65 |
| 5,366,896 A | * | 11/1994 | Margrey et al. | .............. 436/48 |
| 5,428,690 A | * | 6/1995 | Bacus et al. | ................. 382/128 |
| 5,499,097 A | * | 3/1996 | Ortyn et al. | ................. 356/615 |
| 5,548,661 A | * | 8/1996 | Price et al. | .................. 382/133 |
| 5,587,833 A | * | 12/1996 | Kamentsky | ................. 359/393 |
| 5,699,794 A | * | 12/1997 | Fleck | .......................... 600/310 |
| 6,355,487 B2 | * | 3/2002 | Kowallis | ...................... 436/44 |

FOREIGN PATENT DOCUMENTS

| | | |
|---|---|---|
| JP | 3-285175 | 12/1991 |
| JP | 10-49201 | 2/1998 |

* cited by examiner

*Primary Examiner*—Yon J. Couso
(74) *Attorney, Agent, or Firm*—Nixon & Vanderhye

(57) ABSTRACT

A specimen processing system according to the present invention includes a plurality of specimen processing units each having flat sides and a specimen operating surface and operated singly. The specimen processing units have at least the same depth dimension, and the specimen operating surfaces of the specimen processing units have the same height dimension. The system further includes a coupling section for closely coupling the right and left sides of the specimen processing units to each other and a single driving control unit for controlling a related operation of all of the specimen processing units coupled to each other by the coupling section and a single operation of a designated one of the specimen processing units.

4 Claims, 2 Drawing Sheets

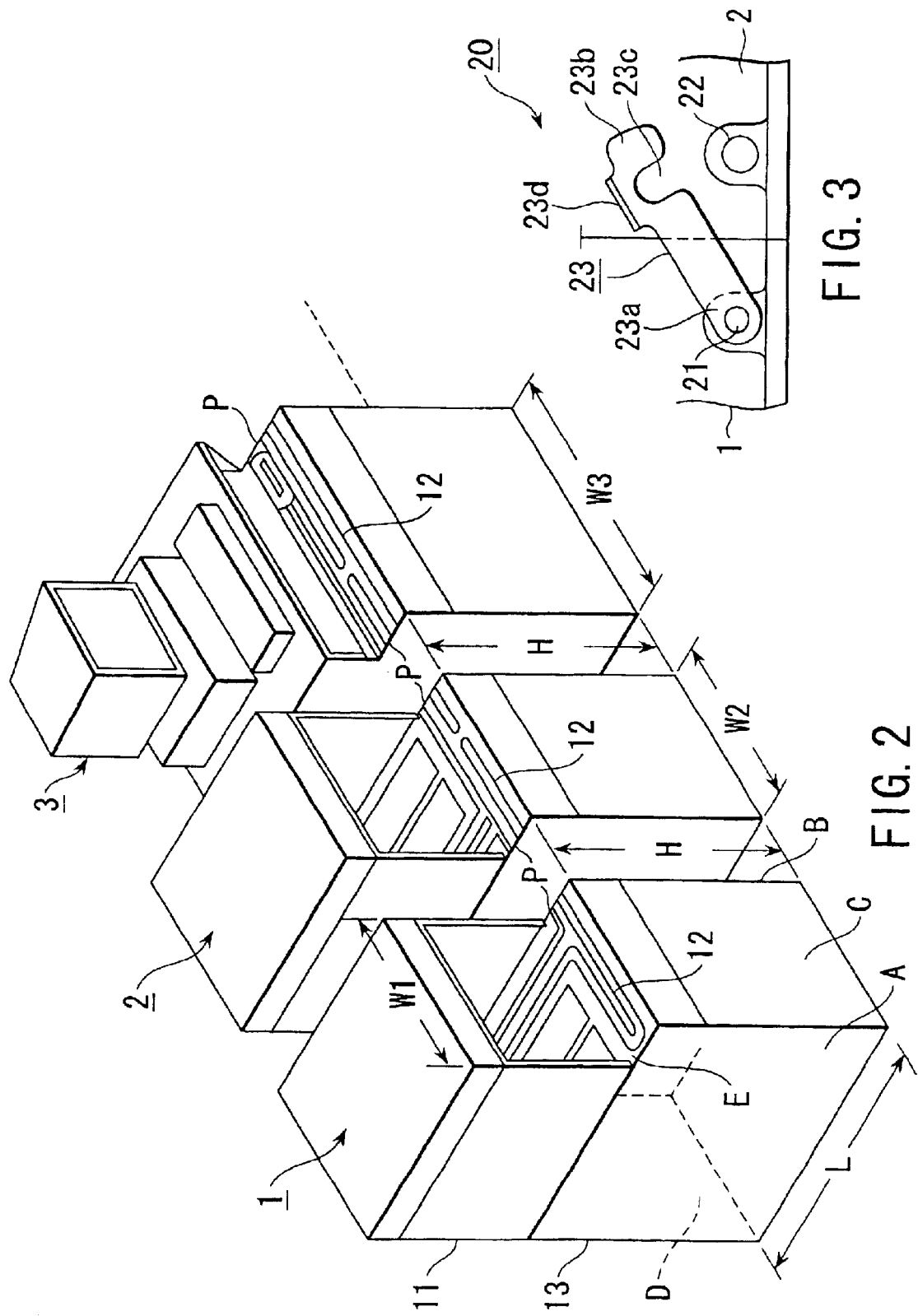

SPECIMEN PROCESSING SYSTEM

CROSS-REFERENCE TO RELATED APPLICATIONS

This application is based upon and claims the benefit of priority from the prior Japanese Patent Application No. 2000-189659, filed Jun. 23, 2000, the entire contents of which are incorporated herein by reference.

BACKGROUND OF THE INVENTION

The present invention relates to a specimen processing system for executing a process such as sampling and slide sampling creation for a specimen of blood or the like.

Conventional specimen processing systems are configured independently of one another according to a purpose of processing a specimen (e.g., blood). Different processing systems should therefore be configured if the purposes of processing are slightly different. In other words, it is necessary to prepare specimen processing systems corresponding in number to the processing purposes. If, therefore, there are a large number of processing purposes, high facilities costs and large setting spaces are required for configuring different systems.

In the above conventional specimen processing system, even when an operator wishes to execute only a specific one of specimen processing steps, he or she cannot operate only a section of the system for executing the specific step. In this case, the whole system need to be operated and thus energy is consumed in vain.

BRIEF SUMMARY OF THE INVENTION

An object of the present invention is to provide a specimen processing system having the following advantages:

(a) A plurality of specimen processing units capable of operating singly are coupled to each other. Thus, the processing system can easily be configured in accordance with the purposes of processing by changing the layout of the system.

(b) No processing systems need to correspond in number to the processing purposes. Therefore, no facilities costs are increased or no large setting spaces are required.

(c) Since only a necessary specimen processing unit can be selected and operated, wasted energy consumption can be avoided.

In order to attain the above object, the specimen processing system according to the present invention is configured as follows:

A specimen processing system according to one aspect of the present invention comprises a plurality of specimen processing units each having flat sides and a specimen operating surface and operated singly, the specimen processing units having at least a same depth dimension, and the specimen operating surfaces of the specimen processing units having a same height dimension, coupling means for closely coupling right and left sides of the specimen processing units to each other, and a single driving control unit for controlling a related operation of all of the specimen processing units coupled to each other by the coupling means and a single operation of a designated one of the specimen processing units.

In the specimen processing system, the specimen processing units each includes a unit housing having right and left sides parallel to each other and a specimen operating surface perpendicular to the right and left sides and parallel to a ground, the specimen operating surface is located at a set height from the ground, a specimen carry-in/carry-out lane formed on the specimen operating surface and having a predetermined lane structure, one end of the specimen carry-in/carry-out lane facing at least one of the right and left sides, and a unit body for processing a specimen carried into the unit housing through the specimen carry-in/carry-out lane, the processed specimen being carried out through the specimen carry-in/carry-out lane.

In the specimen processing system, the unit housing further has front and back sides parallel to each other and perpendicular to the right and left sides.

In the specimen processing system, the coupling means is a free-coupling/separation type coupling mechanism including at least one of a mechanical coupling mechanism and a magnetic coupling mechanism.

In the specimen processing system, the single driving control unit includes a pneumatic driving section and a control section and is coupled to one of the plurality of specimen processing units.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 2 is a perspective view showing an outward appearance of three typical specimen processing units that are separated from the specimen processing system according to the embodiment of the present invention; and FIG. 3 is a side view showing an example of a coupling mechanism for coupling the specimen processing units of the specimen processing system according to the embodiment of the present invention.

DETAILED DESCRIPTION OF THE INVENTION

Embodiment

Figure 1:
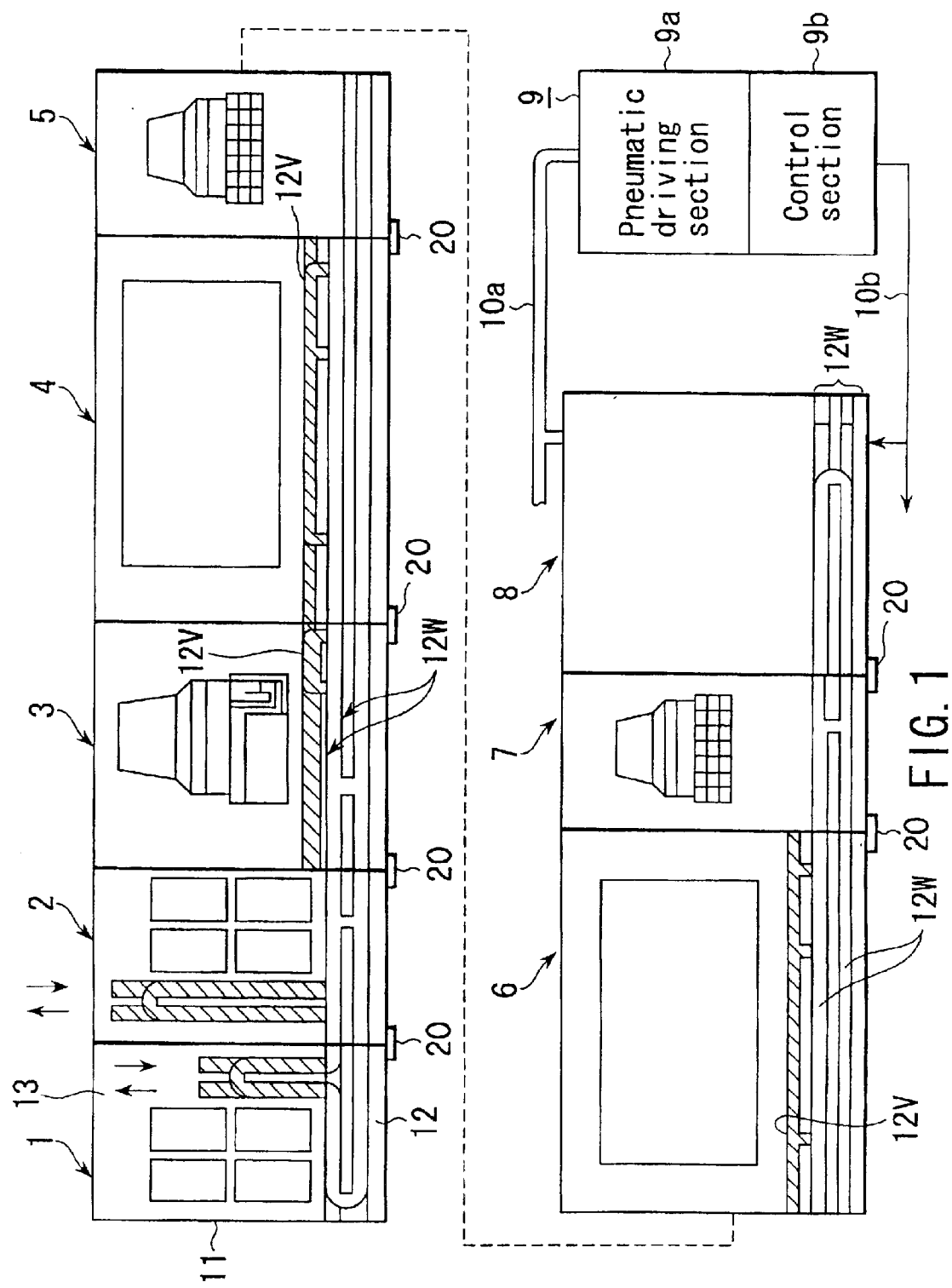
FIG. 1 is a top view showing a layout of a specimen processing system according to an embodiment of the present invention.

In FIGS. 1 and 2, reference numerals 1 to 8 indicate specimen processing units of a specimen processing system according to an embodiment of the present invention. Each of the units 1 to 8 includes a unit housing 11, a specimen carry-in/carry-out lane 12, and a unit body 13.

The unit housing 11 has right and left sides B and A parallel to each other and front and back sides C and D parallel to each other and perpendicular to the right and left sides B and A. The unit housing 11 also has a specimen operating surface E located at a fixed height H from the ground. The surface E is perpendicular to the right and left sides B and A and parallel to the ground.

The unit housing 11 has a depth dimension L that is set at a specific value and a width dimension W. The unit housings of the respective units have different width dimensions. In this embodiment, however, the width dimensions W1 and W2 in the units 1 and 2 are the same.

The specimen carry-in/carry-out lane 12 is formed on the specimen operating surface E with its end facing at least one of the right and left sides B and A of the unit housing 11. The lane 12 has a predetermined lane structure (shape, dimension, layout, etc.).

The unit body 13 can be operated singly. The unit body 13 processes a specimen that is carried into the unit housing 11 through the specimen carry-in/carry-out lane 12. The processed specimen is automatically carried out of the unit body 13 through the processed specimen.

A coupling mechanism 20 is provided on the right and left sides B and A or on the front and back sides C and D in order to closely couple the right and left sides of adjacent specimen processing units to each other. A free-coupling/separation type coupling mechanism, such as a mechanical coupling mechanism for mechanically coupling the units and a magnetic coupling mechanism for magnetically coupling the units is used as the coupling mechanism 20.

FIG. 3 illustrates the coupling mechanism 20 as an example of the mechanical coupling mechanism. In this mechanism 20, one end 23a of a coupling lever 23 is rotatably supported by a shaft pin 21 provided at one specimen processing unit, e.g., the unit 1, and a fitting recess portion 23c of the other end 23b of the lever 23 is freely fitted to and separated from a fastening pin 22 provided at another specimen processing unit, e.g., the unit 2. In FIG. 3, reference numeral 23d indicates a lever operating knob.

In the specimen processing system described above, the specimen processing units 1 to 8 that can be operated solely are arranged according to a purpose of processing and coupled to each other by means of the coupling mechanism 20. In this arrangement, the ends P of the specimen carry-in/carry-out lanes 12 of the respective units 1 to 8 are coupled to each other, thus forming one continuous lane in the whole of the system. Each of the specimen processing units 1 to 8 will now be described more specifically.

Referring to FIG. 1, reference numeral 1 denotes a stock unit, 2 a start unit, 3 a CLA control unit, 4 a hematology-analyzer main unit, 5 a hematology-analyzer auxiliary unit, 6 another hematology-analyzer main unit, 7 another hematology-analyzer auxiliary unit, and 8 a slide sample making unit.

The stock unit 1 can stock, e.g., 200 specimens at the same time. The specimens can be sorted according to their purposes and types. The stock unit 1 has an automatic rack rising mechanism (not shown) and is so designed friendly that an operator can easily load/unload specimen racks into/from the stock unit 1. The unit 1 also has an emergency stop mechanism (not shown) for automatically stopping an operation of the stock unit 1 and protecting an operator when the operator carelessly reaches into the unit 1 with hand during the operation of the system. Some stock units can be added when the need arises.

Like the above stock unit 1, the start unit 2 can stock, e.g., 200 specimens at the same time. The start unit 2 selectively starts an automatic rack loading operation (for a large number of specimens) and a manual rack loading operation (for emergency/a small number of specimens). Further, like the stock unit 1, the start unit 2 has an automatic rack rising mechanism and an emergency stop mechanism, and some units can be added. The unit 2 is so constituted that it can start processing a specimen from a given specimen rack.

The CAL control unit 3 can display the status of specimens and the system and monitor the whole of the system. The unit 3 can also provide an instruction to unload specified specimens and move them to their respective devices separately. Moreover, the unit 3 can perform the following operations: automatic re-inspection, address management of the stock unit 1, an instruction to connect units (on-line) and disconnect them (off-line), and an instruction to move a specimen to a specified position based on order information from a host computer (not shown).

The hematology-analyzer main unit 4 can perform an original operation of a hematology analyzer. More specifically, the main unit 4 can perform a CLA-mode operation (95 specimens per hour at the maximum: CBC+Diff mode), a primary-mode operation (110 specimen per hour at the maximum: CBC+Diff mode), a secondary-mode operation (which can be performed any time during the CLA-mode operation). Units can be added to the unit 4 according to the number of specimens. The unit 4 can hold a reagent in its front portion and a compressor in its back portion. When an aspiration error occurs in a specimen, the unit 4 can inspect the specimen and separate it from the others at once. In other words, a specimen that is likely to coagulate, a specimen whose volume is lower than a prescribed one, a specimen with a very low value of Hgb are detected and separated from the others immediately. An operator can thus provide a suitable instruction to the unit 4.

The hematology-analyzer auxiliary unit 5 can compactly hold a keyboard, a mouse, and the like.

The hematology-analyzer main unit 6 is the same as the hematology-analyzer main unit 4 described above.

The hematology-analyzer auxiliary unit 7 is the same as the hematology-analyzer auxiliary unit 5.

The slide sample making unit 8 is able to make a slide sample in real time. Adopting a centrifugal smear method, the unit 8 can make a more uniform sample. Further, the unit 8 can automatically select a sample making condition based on the results of analysis of the hematology analyzer. The unit 8 can be on-line connected to an automatic hemogram analyzing device. The unit 8 can perform a connecting operation (on-line operation) of units and a disconnecting operation (off-line operation) thereof.

A drive control unit 9, which does not function as a so-called specimen processing unit of the present invention, is coupled to the specimen processing units 1 to 8 to make the units 1 to 8 interact with one another and operate a specified unit singly. The unit 9 is constituted of a pneumatic driving section 9a and a control section 9b. The pneumatic driving section 9a includes an air compressor, an air dryer and an air tank and can supply compressed air necessary for driving the system to the respective units 1 to 8 through an air pipe 10a. The control section 9b exercises sequence control and other electric control through a signal line 10b in order to supply compressed air to the units 1 to 8 by the pneumatic driving section 9a.

The following are descriptions of specific operations of the specimen processing units described above.

a) In the stock unit 1, when an operator sets specimen-contained test tubes (not shown) in a rack, the rack is moved to the start unit 2.

b) When the operator depresses a start button (not shown) of the start unit 2, the specimen-contained test tubes are removed from the rack by an operation arm (not shown) and placed on the lane 12. As a result, the test tubes are conveyed on the lane 12 by a conveyor belt (not shown).

c) When the test tubes reach the CLA control unit 3, a bar code reader (not shown) of the unit 3 reads a bar code from each of the test tubes. If a bar code error is detected from a test tube, the test tube is led to a lead-in lane 12V. Normal specimen-contained test tubes go straight on the main lane 12W.

d) When the specimen-contained test tubes arrive at the hematology-analyzer main unit 4, a bar code reader (not shown) of the unit 4 reads the bar codes of the test tubes. If a request to inspect the specimen-contained test tubes is made, they are equally sorted in consideration of a jam on the lane and an off-line operation. The test tubes led to the lead-in lane 12V are subjected to sampling. If a request to inspect a test tube is issued when the hematology-analyzer main unit 4 is full, the test tube passes through the unit 4 without stopping and retreats to the stock unit 1 temporally. After a lapse of a fixed period of time, the test tube is automatically returned to the main lane 12W.

e) The bar codes of the specimen-contained test tubes arrived at the hematology-analyzer auxiliary unit 5 are read out.

f) The hematology-analyzer main unit 6 performs the same operation as that of the hematology-analyzer main unit 4.

g) The hematology-analyzer auxiliary unit 7 performs the same operation as that of the hematology-analyzer auxiliary unit 5. If a request to inspect the specimen-contained test tube is made, it is moved to the slide sample making unit 8. If not, it is put on a return lane and returned to the stock unit 1. If a request to inspect a test tube is issued when the slide sample making unit 8 is full, the test tube passes through the unit 8 without stopping and stands by the stock unit 1 temporally. After a lapse of a fixed period of time, the test tube is automatically returned to the main lane 12W.

h) When the specimen-contained test tube returned to the main lane 12W reaches the lead-in lane 12V of the unit 3, its bar code is read out. When a request to re-inspect the test tube is issued or a destination of a specimen-contained test tube, which is not carried into the lead-in lane or the slide sample making unit 8 because it is full of test tubes, is open, the test tube is returned to the main lane 12W, and a series of operations is repeated.

i) The specimen-contained test tube sent out to the unit 1 is also returned to the lane by the arm if a request to re-inspect the test tube and a series of operations are repeated accordingly.

The features of the above embodiment of the present invention are summarized as follows.

1) The layout of the system can easily be modified.

The right and left sides B and A of the unit housing 11 are parallel to each other, as are the front and back sides C and D. The sides A and B and the sides C and D are perpendicular to each other. The depth dimensions L of the unit housings 11 of the respective units 1 to 8 are the same, as are the height dimensions H of the specimen operating surfaces E of the units 1 to 8, on each of which the specimen carry-in/carry-out lane 12 is formed. Therefore, the units 1 to 8 can be separated and coupled and their layout can properly be modified in accordance with the status of their installation space (linear, L-shaped, U-shaped, etc.). A unit other than the standard units, such as a coagulation analyzing unit, a hemoglobin AIC analyzing unit, and a pre-processing unit, can be added. The system can be connected to a sorting lane capable of handling a variety of blood-collecting tubes at once. The system can also be operated together with biochemistry and immunology. Further, the units having the same function can be increased in number in accordance with the scale of the system.

2) The direction in which a specimen moves can be changed.

By selectively moving the specimen carry-in/carry-out lane 12, a specimen to be processed can be moved on the lane 12 from right to left or from left to right.

3) A specific specimen can be conveyed directly.

A single specific specimen is moved directly to a predetermined target processing unit and can thus be processed in real time.

4) The specimen processing units can be operated singly.

The desired units such as the hematology-analyzer main unit 4 and the slide sample making unit 8 can be operated singly. Thus, the problem that an unnecessary processing unit is operated at the same time when a desired processing unit is done, can be eliminated and wasted energy consumption can be avoided.

5) A specific specimen can be carried in again.

The system has a program for instructing to carry in a specimen again. Therefore, when a specimen cannot be carried into a given specimen processing unit accidentally, it can be carried into another processing unit automatically.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A specimen processing system comprising:
 a plurality of specimen processing units each having flat sides and a specimen operating surface and operated singly, the specimen processing units having at least a same depth dimension, and the specimen operating surfaces of the specimen processing units having a same height dimension;

coupling means for closely coupling right and left sides of the specimen processing units to each other; and a single driving control unit for controlling a related operation of all of the specimen processing units coupled to each other by the coupling means and a single operation of a designated one of the specimen processing units;

each said specimen processing unit including:

a unit housing having right and left sides parallel to each other said specimen operating surface being perpendicular to the right and left sides of said unit housing parallel to a around surface, and located at a set height above the around surface;

a specimen carry-in/carry-out lane formed on said specimen operating surface and having a predetermined lane structure, one end of the specimen carry-in/carry-out lane facing at least one of the right and left sides; and a unit body for processina a specimen carried into the unit housing through the specimen carry-in/carry-out lane, the processed specimen being carried out through the specimen carry-in/carry-out lane.

2. The specimen processing system according to claim 1, wherein the unit housing further has front and back sides parallel to each other and perpendicular to the right and left sides.

3. The specimen processing system according to claim 1, wherein the coupling means is a free-coupling/separation type coupling mechanism including at least one of a mechanical coupling mechanism and a magnetic coupling mechanism.

4. The specimen processing system according to claim 1, wherein the single driving control unit includes a pneumatic driving section and a control section and is coupled to one of the plurality of specimen processing units.

* * * * *